United States Patent [19]

Steinbuch et al.

[11] Patent Number: 5,198,534
[45] Date of Patent: Mar. 30, 1993

[54] PROCESS FOR PREPARATION OF ACTIVATED PROTEIN C BY IMMOBILIZED APROTININ CHROMATOGRAPHY

[75] Inventors: Marion Steinbuch, Voisin le Bretonneux; Jacques Chabbat, Paris; Olivier Taby, Antony, all of France

[73] Assignee: Fondation Nationale de Transfusion Sanguine, Paris, France

[21] Appl. No.: 613,843

[22] PCT Filed: Apr. 10, 1990

[86] PCT No.: PCT/FR90/00258

§ 371 Date: Jan. 9, 1991

§ 102(e) Date: Jan. 9, 1991

[87] PCT Pub. No.: WO90/12028

PCT Pub. Date: Oct. 18, 1990

[30] Foreign Application Priority Data

Apr. 12, 1989 [FR] France .............................. 89 04814
Feb. 20, 1990 [FR] France .............................. 90 02028

[51] Int. Cl.$^5$ .............................................. C07K 3/20
[52] U.S. Cl. .................................... 530/381; 530/380; 530/413
[58] Field of Search ............... 530/381, 382, 383, 384, 530/413, 380

[56] References Cited

U.S. PATENT DOCUMENTS 4,604,285 8/1986 Smith et al. ......................... 530/380
4,849,403 7/1989 Stocker et al. ...................... 530/381

FOREIGN PATENT DOCUMENTS 0287028 4/1988 European Pat. Off. .
WO85/00521 2/1985 PCT Int'l Appl. .

OTHER PUBLICATIONS

Cooper, T. G., "The Tools of Biochemistry". 1977. John Wiley & Sons, New York. pp. 234-255.
Freifelder, D. "Physical Biochemistry. Applications to Biochemistry and Molecular Biology". 1976. W. H. Freeman & Co., San Francisco. pp. 204-205.
Espana et al. (Dec. 15, 1989). Aprotinin is a competitive inhibitor of activated protein C. Thrombosis Res. 56: 751-756.
Griffin, J. H. et al., Aprotinin (Trasylol) is a Competitive Inhibitor of Activated Protein C. Thrombosis and Haemostasis, Abstracts-XIIth Congress of the International Society of Thrombosis and Haemostasis, Tokyo, Japan, vol. 62, p. 385, abstract No. 1212 (Aug. 1989).
Thrombosis and Haemostasis, Abstracts-XIIth Congress of the International Society of Thrombosis and Haemostasis, Tokyo, Japan, vol. 62, p. 272, abstract Nos. 870 to 873 (Aug. 1989).

Primary Examiner—Robert A. Wax
Assistant Examiner—Richard C. Ekstrom
Attorney, Agent, or Firm—Finnegan, Henderson, Farabow, Garrett & Dunner

[57] ABSTRACT

The present invention relates to a method for preparing activated protein C (APC) from a sample containing the said activated protein C, characterized in that the activated protein C is bound to insolubilized aprotinin and then in that, after washing of the said activated protein C/aprotinin complex with a buffered saline solution, the said activated protein C is collected by elution with an acidic aqueous solution or a solution containing a chaotropic agent.

The invention also relates to the activated protein C thereby obtained according to the method described above.

14 Claims, No Drawings

PROCESS FOR PREPARATION OF ACTIVATED PROTEIN C BY IMMOBILIZED APROTININ CHROMATOGRAPHY

The present invention relates to a method for preparing activated protein C (APC).

Protein C is a plasma glycoprotein whose active form is a serine protease (1, 2).

Human protein C is a protein of molecular weight 62,000 consisting of two chains: a heavy chain of molecular weight 41,000 bearing the active site and a light chain of molecular weight 21,000, linked via a disulphide bridge (2). Its plasma concentration is 3-5 mg/l.

Like other proteins, especially plasma proteins, this protein is a vitamin K-dependent factor. It is synthesized by the liver in the form of a precursor. The first 11 glutamic acids of the light chain are carboxylated at the gamma-position by a liver carboxylase having a vitamin K as a cofactor (3). These gamma-carboxy-glutamic residues are involved in an interaction with calcium ions (4). Since phospholipids are negatively charged, calcium produces an ionic bridge between these compounds and the appropriate region of vitamin K-dependent factors The light chain possesses, moreover, a beta-hydroxyaspartic residue which also appears to be involved in the interaction with $Ca^{++}$.

The proenzyme is converted to activated protein C (APC) by cleavage of a dodecapeptide in the N-terminal portion of the heavy chain (2). This reaction, which takes place in the microcirculation, is catalyzed in the presence of calcium by a 1:1 stoichiometric complex formed between thrombin and a protein located at the surface of the endothelial cells, thrombomodulin (5).

The active form has an anticoagulant action by inactivating the coagulation cascade cofactors V and VIII by limited proteolysis (6). The active enzyme also appears to increase fibrinolysis by activating tissue plasminogen activator inhibitor.

APC exercises its activity fully only in the presence of a cofactor, protein S, phospholipids and calcium. Protein S is also a vitamin K-dependent plasma glycoprotein. It is a single-chain protein, of MW 75,000, its plasma concentration being 25 mg/l. It circulates to the extent of 50% in free form and 50% in the form of a non-covalent complex with a protein of the complement system, "C4-Binding Protein" (C4BP) (7). When protein S is linked to C4BP, it cannot act as a cofactor (7).

In contrast to the other vitamin K-dependent enzymes, protein C is anticoagulant.

Congenital and acquired protein C deficiencies are known. In this case, as with AT III deficiencies, a tendency to repeated thrombotic accidents is observed.

The therapeutic use of the enzyme and the proenzyme is advantageous. Thus, protein C may be used for the treatment of protein C deficiencies, and especially in homozygotic neonates who develop purpura fulminans.

This often fatal disease is characterized by substantial thrombotic lesions which necessitate therapy with protein C-enriched plasma concentrates. The heterozygotic form can lead to mild to severe thrombotic episodes, or may be totally asymptomatic.

Both protein C and activated protein C may be employed for the prophylaxis and treatment of venous and arterial thromboses, pulmonary, cerebral and cardiac embolisms, CIVD and septic shock.

Activated protein C may also be used for the replacement of traditional anticoagulants (especially heparin) without their side effects in arterial or venous thromboses, surgery and phlebitis, and in the case of reocclusion of myocardial infarctions.

Great structural homology exists between certain vitamin K-dependant factors, and especially between factors VII, IX and X and protein C. They have, in addition, a very similar molecular weight (56,000, 57,000, 59,000 and 62,000, respectively).

The similarity of these molecular features hence causes difficulties in the isolation of these different factors.

The object of the present invention is specifically to overcome this obstacle and to propose a method enabling activated protein C to be obtained rapidly from a blood fraction enriched to a greater or lesser extent in protein C.

It was, in effect, demonstrated by the inventors that aprotinin, which is a polypeptide of animal origin of 58 amino acids, inhibits APC. Since the interaction is reversible, it was possible to purify APC on insolubilized aprotinin.

More especially, the present invention relates to a method for preparing activated protein C from a starting material containing the said activated protein, characterized in that the activated protein C is adsorbed on insolubilized aprotinin and then in that, after washing of the said APC/aprotinin complex with a buffered saline solution, the said activated protein C is collected by elution with an acidic aqueous solution or a solution of a chaotropic agent.

The starting material containing protein C can originate from various sources. These can be different fractions obtained by the technologies of blood fractionation, for example the material can be the so-called PPSB fraction, or fractions such as PPSB pre-eluate, fractions obtained during ethanol fractionaction or fractions obtained by prior purification, either by immunopurification as is, for example, described in European Patent No. 138,222, or fractions enriched in protein C as are described, for example, in British Journal of Haematology, 1988, 70, 436-440.

According to a particular embodiment of the invention, the starting material is a concentrate of prothrombin complex. The protein C present in this concentrate is activated therein by thrombin which is generated in the said starting material by adding calcium, this calcium being subsequently removed so as to permit activation of the protein C by the thrombin generated in situ. In this case, the calcium is added to the starting material at a concentration of between 10 and 100 mM, and is then removed therefrom by dialysis or diafiltration.

The binding of the APC is preferably performed at a pH of between 7 and 9, in general at an optimum pH of 8 to 8.4, with a suitable ionic strength but not exceeding 0.4M NaCl, and preferably of less than 0.25M NaCl.

The complex thereby formed between aprotinin and APC is sufficiently stable to be subjected to a pre-elution with saline solutions without the APC being detached.

To elute the APC, elution conditions dissociating the complex should be adopted, in particular extremes of pH, especially pH values of between 1 and 3. The activated protein C may also be collected by elution with a solution containing a chaotropic agent, for example KSCN or NaSCN. The chaotropic agent will then be removed by dialysis.

The complexing reaction is very specific and the eluted product is free from factor II, factor VII, factor IX and factor X, this being the case when the starting material is the PPSB fraction, and the yield being very satisfactory.

As stated above, the fraction treated must contain protein C in activated form; this activation may be performed in different ways, either using thrombin, or using the specific activator of protein C extracted from snake venom, or alternatively the natural activator consisting of thrombin and thrombomodulin.

Some fractions may already contain protein C in activated form; in this case, activation will obviously be unnecessary.

The examples below are designed to demonstrate other advantages and features of the present invention.

EXAMPLE 1

The starting material used for this example is a protein C obtained by immunopurification.

Immunopurification of protein C:

A plasma subfraction enriched in protein C is adsorbed on a column of anti-protein C monoclonal antibodies insolubilized on cyanogen bromide-activated Sepharose 4B (Pharmacia). The monoclonal antibody employed recognizes protein C and does not recognize APC.

A pre-elution is performed with 50 mM Tris-HCl buffer pH 8, 0.5M NaCl. Elution is carried out with 3M potassium thiocyanate solution. The eluate obtained is concentrated and dialysed to 75 mM NaCl buffered to pH 8.

A solution of protein C is thereby obtained, and both the ratio of antigen to protein concentration and SDS-PAGE electrophoresis show a high degree of purification.

The proenzyme is activated with one of the known activators: thrombin/thrombomodulin, thrombin, Agkistrodon contortrix or Russel's viper venom. These activators can be added to the fraction in solution or can be insolubilized on a matrix. In the latter case, the activation is carried out batchwise or on a column.

2 ml of activated immunopurified protein C are placed on a column (1×5) of aprotinin-Sepharose 4B (Pharmacia) (5 mg of aprotinin per ml of gel) equilibrated with 50 mM Tris-HCl buffer pH 8, 75 mM NaCl.

A pre-elution is carried out with 50 mM Tris-HCl buffer pH 8, 0.5M NaCl.

The APC is by lowering the pH with 0.1N HCl solution, and the pH is brought back at once to 8.

Assay of the amidolytic activity, the coagulant activity and also Laurell anti-protein C one-dimensional immunoelectrophoresis show that activated protein C is to be found only in the HCl eluate.

EXAMPLE 2

The starting material used for this second example is a concentrate of the prothrombin complex (PPSB). The protein C contained in this preparation is activated with an activator as for Example 1.

100 ml of starting material are placed on a column (1×5) of aprotinrn-Sepharose 4B (Pharmacia) (5 mg of aprotinin per ml of gel) equilibrated with 50 mM Tris-HCl buffer pH 8, 0.15M NaCl.

A pre-elution is performed with 50 mM Tris-HCl buffer pH 8, 0.5M NaCl.

No activated protein C activity is detectable in the fraction not retained or in the 0.5M NaCl pre-elution.

The APC specifically retained on the matrix is eluted by lowering the pH with 0.1N HCl solution. The pH is immediately brought back to 8.

The eluted fraction has the properties of of APC from the standpoint of both biological activity and of electrophoretic behaviour and antigenicity. The techniques used are assays of anticoagulant and amidolytic activities, immunological identifiction and SDS-PAGE electrophoresis with and without a reducing agent.

EXAMPLE 3

Calcium chloride (25 mM final) is added to the so-called PPSB fraction of a concentrate of the prothrombin complex. After gentle agitation for 30 minutes to 4 hours, the calcium is removed by dialysis or by diafiltration against a buffer containing, for example, 50 mM Tris-HCl, 0.15M NaCl, pH 7.4.

Activation of the protein C is subsequently performed with gentle agitation at room temperature or at 4° C. for 8 to 24 hours.

The fraction thereby obtained is placed on aprotinin-Sepharose in order to purify the activated protein C.

This purification of the activated protein C is carried out according to the method described above.

BIBLIOGRAPHY

1) Stenflo J., (1976), J. Biol. Chem. 251, 355–363
2) Kisiel W., (1979), J. Clin. Invest. 64, 761–769
3) Ferlund P. and Stenflo J., (1982), J. Biol. Chem. 257, 12170–12179
4) Nelsestuen G. L., Kisiel W. and Di Scipio R. G., (1978), Biochemistry 17, 2134–2138
5) Esmon C. T. and Owen W. G., (1981), Proc. Natl. Acad. Sci. USA. 78, 2249–2252
6) Walker P. J., Sexton P. W. and Esmon C. T., (1979), Biochim Biophys. Acta 571, 333–342
7) Dahlbäck B., (1986) J. Biol. Chem, 261, 12022–12027

We claim:

1. A method for preparing activated protein C from a starting material containing said activated protein C, comprising:
   (a) absorbing activated protein C on insolubilized aprotinin;
   (b) washing the resulting absorbed activated protein C; and
   (c) eluting activated protein C from said insolubilized aprotinin with a solution selected from the group consisting of an acid solution and a solution of a chaotropic agent.

2. The method of claim 1, wherein said absorbed activated protein C is washed with a buffered saline solution.

3. The method of claim 2, wherein said absorbed activated protein C is washed with a buffered saline solution having a pH of about 8.

4. The method of claim 1, wherein said activated protein C is absorbed on insolubilized aprotinin at a pH between 7 and 9.

5. The method of claim 4, wherein said activated protein C is absorbed on insolubilized aprotinin at a pH between 8 and 8.4.

6. The method of claim 1, wherein activated protein C is eluted by an acidic solution having a pH between 1 and 3.

7. The method of claim 1, wherein activated protein C is eluted with a solution of a chaotropic agent, said chaotropic agent selected from the group consisting of KSCN and NaSCN.

8. The method of claim 7, wherein said chaotropic agent is removed by dialysis.

9. The method of claim 1, wherein said insolubilized aprotinin is aprotinin-agarose 4B.

10. The method of claim 9, wherein the concentration of aprotinin is between 0.5 and 5 mg per ml of agarose.

11. The method of claim 1, wherein said starting material is selected from the group consisting of activated immunopurified protein C and a prothrombin complex (PPSB) treated with an activator of protein C.

12. The method of claim 11, wherein the protein C in said starting material is activated by an activator selected from the group consisting of thrombin/thrombomodulin, thrombin, Agkistrodon contortrix venom and Russel's viper venom.

13. The method of claim 11, wherein the protein C in said prothrombin complex is activated by thrombin generated by the addition of calcium, said calcium being subsequently removed so as to permit activation of protein C by said thrombin.

14. The method of claim 13, wherein said calcium is added at a concentration between 10 and 100 mM.

* * * * *

UNITED STATES PATENT AND TRADEMARK OFFICE
CERTIFICATE OF CORRECTION

PATENT NO. : 5,198,534

DATED : March 30, 1993

INVENTOR(S) : Marion STEINBUCH et al.

It is certified that error appears in the above-identified patent and that said Letters Patent is hereby corrected as shown below:

Claim 9, column 5, line 6, delete "4B".

Signed and Sealed this

Twenty-third Day of November, 1993

Attest:

BRUCE LEHMAN

Attesting Officer

Commissioner of Patents and Trademarks